(12) United States Patent
Hoogenboom et al.

(10) Patent No.: US 10,029,020 B2
(45) Date of Patent: Jul. 24, 2018

(54) FULLERENE COMPOSITIONS

(71) Applicant: UNIVERSITEIT GENT, Ghent (BE)

(72) Inventors: Richard Hoogenboom, Terneuzen (NL); Joachim Van Guyse, Ghent (BE); Victor Retamero De La Rosa, Ghent (BE)

(73) Assignee: Universiteit Gent, Ghent (BE)

( * ) Notice: Subject to any disclaimer, the term of this patent is extended or adjusted under 35 U.S.C. 154(b) by 0 days.

(21) Appl. No.: 15/567,338

(22) PCT Filed: Apr. 22, 2016

(86) PCT No.: PCT/EP2016/058988
§ 371 (c)(1),
(2) Date: Oct. 17, 2017

(87) PCT Pub. No.: WO2016/170100
PCT Pub. Date: Oct. 27, 2016

(65) Prior Publication Data
US 2018/0133344 A1 May 17, 2018

(30) Foreign Application Priority Data
Apr. 23, 2015 (EP) .................................. 15164759

(51) Int. Cl.
| | | |
|---|---|---|
| A61K 47/69 | (2017.01) | |
| C09C 3/10 | (2006.01) | |
| C08K 3/04 | (2006.01) | |
| C01B 32/154 | (2017.01) | |
| C08G 73/02 | (2006.01) | |
| C09C 1/56 | (2006.01) | |
| C01B 32/156 | (2017.01) | |
| A61N 5/06 | (2006.01) | |
| B82Y 5/00 | (2011.01) | |

(52) U.S. Cl.
CPC ...... *A61K 47/6933* (2017.08); *A61K 47/6935* (2017.08); *C01B 32/154* (2017.08); *C01B 32/156* (2017.08); *C08G 73/0233* (2013.01); *C08K 3/045* (2017.05); *C09C 1/56* (2013.01); *C09C 3/10* (2013.01); *A61N 5/062* (2013.01); *B82Y 5/00* (2013.01); *C01P 2004/64* (2013.01)

(58) Field of Classification Search
CPC ............ A61K 47/6933; A61K 47/6935; C08K 3/045; C01B 32/156; C01B 32/154; C08G 73/0233; C09C 1/56; C09C 3/10; A61N 5/062; B82Y 5/00; C01P 2004/64
USPC ........................................................ 428/407
See application file for complete search history.

(56) References Cited

U.S. PATENT DOCUMENTS

| | | | | |
|---|---|---|---|---|
| 6,905,667 B1 * | 6/2005 | Chen | ...................... | B82Y 30/00 423/445 R |
| 7,241,496 B2 * | 7/2007 | Chen | ...................... | B82Y 30/00 423/445 B |
| 7,547,472 B2 * | 6/2009 | Chen | ...................... | B82Y 30/00 423/445 B |
| 2006/0054866 A1 * | 3/2006 | Ait-Haddou | ........... | B82Y 30/00 252/378 R |
| 2009/0203867 A1 * | 8/2009 | Ait-Haddou | ........... | B82Y 30/00 526/259 |
| 2012/0259073 A1 * | 10/2012 | Ait-Haddou | ........... | B82Y 30/00 525/451 |
| 2013/0323188 A1 * | 12/2013 | Kabanov | ................. | A61K 8/84 424/59 |

FOREIGN PATENT DOCUMENTS

| | | | |
|---|---|---|---|
| JP | 2006-069812 | * | 3/2006 |
| JP | 2006-069812 A | | 3/2006 |
| WO | WO2005/100466 | * | 10/2005 |
| WO | WO 2005/100466 A1 | | 10/2005 |
| WO | WO2012/097245 | * | 7/2012 |
| WO | WO 2012/097245 A1 | | 7/2012 |

OTHER PUBLICATIONS

International Preliminary Report on Patentability issued in application No. PCT/EP2016/058988 dated Oct. 24, 2017.

* cited by examiner

*Primary Examiner* — Leszek Kiliman
(74) *Attorney, Agent, or Firm* — Knobbe, Martens, Olson & Bear, LLP

(57) ABSTRACT

Provided herein are fullerene compositions, and methods of preparing fullerene compositions. More particularly, the fullerene compositions include a fullerene-polymer complex having a fullerene and a non-conjugated hydrophilic or amphiphilic polymer. The non-conjugated polymer is substituted with a substituent having a functional group capable of forming intermolecular interactions with the fullerene via pi-stacking.

18 Claims, 1 Drawing Sheet

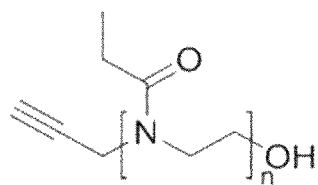
(1)
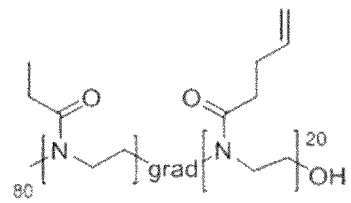
(2)
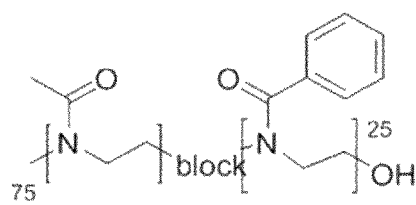
(3)
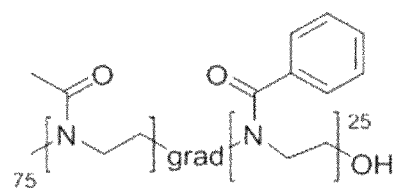
(4)
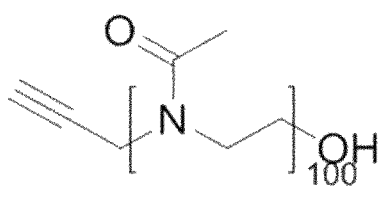
(5)
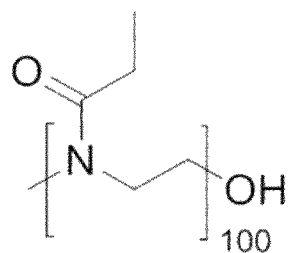
(6)

FULLERENE COMPOSITIONS

FIELD OF THE INVENTION

Provided herein are fullerene compositions, aqueous solutions of said compositions, and methods of preparing thereof. The fullerene compositions can be used in therapy, for example for photodynamic therapy, neuroprotection and as antioxidant.

BACKGROUND OF THE INVENTION

Over the course of the human life, humans are faced with accumulated oxidative damage. This oxidative damage may cause age-related diseases to manifest, such as Parkinson's, Alzheimer's, and certain types of cancer. Prevention of these diseases may be possible by lowering the amount of reactive oxygen species (ROS) in the body. This can partially be achieved by introducing antioxidants. Fullerenes such as buckminsterfullerene ($C_{60}$) possess remarkable antioxidant properties. Moussa et al. (*Biomaterials* 2012, 33, 4936; *Biomaterials* 2012, 33, 6292) have demonstrated that the lifespan of rats could be doubled by regular administration of $C_{60}$. Recent studies suggest that $C_{60}$ administration may prevent the radical cascade in cells, which could lead to an increased lifespan, and to the possible prevention and treatment of cancers and neurodegenerative disorders.

Fullerenes are also promising photosensitizer candidates for use in photodynamic therapy. In photodynamic therapy, a photosensitizer is used which creates singlet oxygen upon local irradiation with light. These singlet oxygen species have toxic effects towards cells and can be used to kill cancer cells. Photodynamic therapy allows for selectively targeting tumor tissue, thereby providing an enhanced selectivity towards cancer cells and fewer side effects compared to radiotherapy and chemotherapy. The current generation of photosensitizers approved by the food and drugs administration (FDA) (Photofrin®, Metvix® and Levulan®) allow only for treatment of the skin or require the patient to stay inside to avoid sun-induced photosensitivity. As $C_{60}$ requires irradiation with UVA-light, early stage cancers could be eliminated using $C_{60}$ and endoscopic irradiation, while collateral damage is minimized by the low penetration depth of the UVA-light and the antioxidant activity of $C_{60}$. Moreover, the low penetration depth of UVA-light and the melanin present in human skin strongly suppress sun-induced photosensitivity. Accordingly, $C_{60}$ may allow for more selective photodynamic therapy compared to the currently used infrared based photodynamic therapy.

Although fullerenes have promising biomedical applications as antioxidant and as photosensitizer, the extremely low water solubility of these compounds results in a low bioavailability. For example, $C_{60}$ has a water solubility of only $10^{-8}$ ng/L.

In general, three approaches are used to increase the water solubility of fullerenes.

A first methodology is the chemical modification of fullerenes to improve their hydrophilicity. However, this is difficult due to poor control of the regioselectivity and causes disruption of the aromaticity, thereby inducing a reduction of the intrinsic beneficial properties of these compounds.

A second methodology is based on the production of meta-stable dispersions of fullerenes, by co-suspension of fullerenes in an organic solvent and water, whereby after slow removal of the organic solvent meta-stable fullerene clusters are obtained. However, this methodology is time-consuming and residual organic solvents can be toxic. Moreover, the biological activity of the clusters decreases with increasing size of the clusters and their meta-stable state only provides stability for a relatively short time.

A third methodology employs water soluble carriers to dissolve or disperse fullerenes in aqueous environment. This approach avoids toxicity issues caused by residual solvent and does not require chemical modification of the fullerenes, while additional functionalities can be incorporated through the carrier. Nevertheless, this approach is typically plagued by instability of the final product or by long purification procedures to remove organic solvents which are used in the preparation of the product. Moreover, the final product typically has a low fullerene content.

Accordingly, there is a need for improved methods for preparing aqueous fullerene compositions, which mitigate at least one of the problems stated above.

SUMMARY OF THE INVENTION

The present inventors surprisingly found that hydrophilic or amphiphilic non-conjugated polymers, which are functionalized with one or more functional groups capable of forming intermolecular interactions with fullerenes via pi-stacking, are particularly effective as carriers to disperse fullerenes in an aqueous environment. More particularly, the present inventors have found that mechanochemical treatment of mixtures of such non-conjugated polymers and fullerenes can lead to the production of fullerene-polymer complexes in the form of well-defined nanoparticles.

Accordingly, provided herein is a composition comprising a fullerene-polymer complex comprising at least one fullerene and a non-conjugated hydrophilic or amphiphilic polymer, said non-conjugated polymer being substituted with at least one substituent comprising a functional group capable of forming intermolecular interactions with said fullerene via pi-stacking.

More particularly, provided herein are the following aspects:

Aspect 1. A composition comprising a fullerene-polymer complex comprising one or more fullerenes and a non-conjugated hydrophilic or amphiphilic polymer, said non-conjugated polymer being substituted with at least one substituent comprising a functional group comprising a carbon-carbon pi-bond interacting with said one or more fullerenes via pi-stacking.

Aspect 2. The composition according to aspect 1, wherein said functional group is selected from the list consisting of allyl, propargyl, phenyl, naphthyl, pyrenyl, vinyl, ethynyl, benzyl, anthryl, indolyl, imidazolyl, thienyl, pyrazinyl, pyrimidinyl, piridazinyl, and triazolyl.

Aspect 3. The composition according to aspect 1 or 2, wherein said non-conjugated polymer is a linear polymer wherein at least one chain end of said linear polymer is provided with said functional group.

Aspect 4. The composition according to any one of aspects 1 to 3, wherein said polymer is selected from the list consisting of polyvinylpyrrolidone (PVP), poly(ethylene glycol) (PEG), a polymer produced from a cyclic imino ether, polyvinyl alcohol (PVA), a dextran, polyglutamic acid (PGA), a poly(oligoethylene glycol acrylate) (POEGA), a poly(oligoethylene glycol methacrylate) (POEGMA), poly [N-(2-hydroxypropyl)methacrylamide] (PHPMA), and copolymers thereof.

Aspect 5. The composition according to any one of aspects 1 to 4, wherein said fullerene-polymer complex is provided as particles having an average size between 25 nm and 100 nm as measured via dynamic light scattering.

Aspect 6. The composition according to any one of aspects 1 to 5, wherein the fullerene:polymer molar ratio of said one or more fullerenes and said polymer within said composition is between 0.1 and 10.

Aspect 7. The composition according to any one of aspects 1 to 6, wherein said fullerene-polymer complex is suspended in an aqueous solvent, and wherein said composition comprises at least 1 wt % of said one or more fullerenes.

Aspect 8. The composition according to any one of aspects 1 to 7, wherein said one or more fullerenes comprise at least 90wt % $C_{60}$.

Aspect 9. A composition according to any one of aspects 1 to 8, for use in medicine.

Aspect 10. A composition according to any one of aspects 1 to 8, for use in treating oxidative damage-related diseases and disorders, preferably selected from the group comprising: Parkinson's disease, Alzheimer's disease, cardiovascular diseases, and cancer.

Aspect 11. Use of a composition according to any one of aspects 1 to 8 as an antioxidant, preferably in food supplements, personal care products; and/or cosmetics.

Aspect 12. A method for the preparation of the composition according to any one of aspects 1 to 8, comprising:
(a) providing one or more fullerenes and a non-conjugated hydrophilic or amphiphilic polymer, said non-conjugated polymer being substituted with at least one substituent comprising a functional group comprising a carbon-carbon pi-bond capable of interacting with said fullerene via pi-stacking; and
(b) mechanochemically treating said fullerene and said non-conjugated polymer, thereby obtaining a fullerene-polymer complex.

Aspect 13. The method according to aspect 12, wherein step (b) comprises milling said fullerene and said polymer.

Aspect 14. The method according to aspect 12 or 13, wherein said non-conjugated polymer is a linear polymer wherein at least one chain end of said linear polymer is provided with said functional group.

Aspect 15. The method according to any one of aspects 12 to 14, wherein said functional group is selected from the list consisting of allyl, propargyl, phenyl, naphthyl, and pyrenyl.

Aspect 16. The method according to any one of aspects 12 to 15, wherein step (b) is performed in the absence of solvents.

Aspect 17. Use of a non-conjugated polymer for increasing the solubility of fullerenes in water, wherein said non-conjugated polymer is substituted with at least one substituent comprising a functional group comprising a carbon-carbon pi-bond capable of interacting with said fullerene via pi-stacking.

The methods for preparing fullerene-polymer compositions described herein can allow for a straightforward, efficient, solvent-free, and highly reproducible preparation of fullerene compositions having a high solubility in water. Moreover, dispersions of the fullerene compositions in water can be stable for weeks or longer. This makes these methods and compositions highly attractive for the preparation of fullerene formulations for biomedical purposes.

The above and other characteristics, features and advantages of the concepts described herein will become apparent from the following detailed description, which illustrates, by way of example, the principles of the invention.

BRIEF DESCRIPTION OF THE DRAWINGS

The drawings depicted herein are merely for illustrative purposes and are not to be seen as limiting the invention in any particular way.

FIG. 1 Overview of a number of polymer types (1-6) used for testing particular embodiments of the method described herein.

DETAILED DESCRIPTION OF THE INVENTION

While potentially serving as a guide for understanding, any reference signs in the claims shall not be construed as limiting the scope thereof.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" when referring to recited components, elements or method steps also include embodiments which "consist of" said recited components, elements or method steps.

Furthermore, the terms first, second, third and the like in the description and in the claims, are used for distinguishing between similar elements and not necessarily for describing a sequential or chronological order, unless specified. It is to be understood that the terms so used are interchangeable under appropriate circumstances and that the embodiments described herein are capable of operation in other sequences than described or illustrated herein.

The values as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to ensure one or more of the technical effects envisaged herein. It is to be understood that each value as used herein is itself also specifically, and preferably, disclosed.

The recitation of numerical ranges by endpoints includes all numbers and fractions subsumed within the respective ranges, as well as the recited endpoints.

All documents cited in the present specification are hereby incorporated by reference in their entirety.

Unless otherwise defined, all terms used in disclosing the concepts described herein, including technical and scientific terms, have the meaning as commonly understood by one of ordinary skill in the art. By means of further guidance, definitions for the terms used in the description are included to better appreciate the teaching of the present disclosure. The terms or definitions used herein are provided solely to aid in the understanding of the teachings provided herein.

The term "fullerene" as used herein refers to an allotropic form of carbon in which the carbon atoms are present in even numbers and are arranged at the vertices of a closed hollow cage-like structure, typically having a roughly spherical shape. Exemplary fullerenes include, but are not limited to $C_{60}$, $C_{70}$, $C_{76}$, $C_{78}$, $C_{82}$, $C_{84}$, $C_{90}$, $C_{96}$, and $C_{120}$. The most stable fullerenes are $C_{60}$ and $C_{70}$. $C_{60}$ comprises 12 pentagons and 20 hexagons, forming a truncated icosahedron. The term "fullerene" as used herein includes fullerenes wherein one or more carbon atoms may be bonded to additional atoms or functional groups. The term "fullerene" as used herein also includes metallofullerenes, i.e. compounds composed of one or more metal atoms which are encapsulated inside a fullerene molecule.

The term "hydrophilic" as used herein means that a compound, polymer, polymer block, or monomer has an affinity for water and which is not capable of forming a macroscopic two-phase solution in distilled water at 25° C. at a concentration of 1% by weight. The term "hydrophilic" as used herein also means water-soluble. Accordingly, the term "water-soluble" refers to the ability of a compound, composition, polymer, polymer block, or monomer, when introduced into water at a concentration equal to 1% by weight, to result in a macroscopically homogeneous solution or dispersion.

The term "hydrophobic" as used herein refers to a compound, polymer, polymer block, or monomer which has a poor solubility in water, when compared to hydrophilic substances. More particularly, the term "hydrophobic" refers to a solubility in water of less than 1% by weight.

The term "amphiphilic polymer" as used herein refers to a polymer, more particularly a copolymer, which comprises at least one hydrophilic part or block and at least one hydrophobic part or block.

As used herein, the terms "suspension", "solution", and "dispersion" (when referring to an aqueous composition comprising fullerenes) are used interchangeably.

The term "aqueous" as used herein means that more than 50 wt % (percent by weight) of the solvent is water. Aqueous compositions or dispersions may further comprise organic liquids which are miscible with water.

The term "$C_{1-12}$alkyl", as a group or part of a group, refers to a hydrocarbyl group of Formula $C_nH_{2n+1}$ wherein n is a number ranging from 1 to 12. Generally, the alkyl groups comprise from 1 to 12 carbon atoms, for example 1 to 6 carbon atoms. Alkyl groups may be linear, or branched and may be substituted as indicated herein. When a subscript is used herein following a carbon atom, the subscript refers to the number of carbon atoms that the named group may contain. Thus, for example, $C_{1-4}$alkyl means an alkyl of 1, 2, 3 or 4 carbon atoms. Examples of $C_{1-6}$alkyl groups are methyl, ethyl, propyl, isopropyl, butyl, isobutyl, sec-butyl, tert-butyl, pentyl and its chain isomers, hexyl and its chain isomers.

The term "$C_{2-12}$alkenyl" by itself or as part of another substituent, refers to an unsaturated hydrocarbyl group, which may be linear, or branched, comprising one or more carbon-carbon double bonds. Preferred alkenyl groups thus comprise between 2 and 12 carbon atoms, preferably between 2 and 6 carbon atoms. Non-limiting examples of $C_{2-12}$alkenyl groups include ethenyl, 2-propenyl, 2-butenyl, 3-butenyl, 2-pentenyl and its chain isomers, 2-hexenyl and its chain isomers, 2,4-pentadienyl and the like.

The term "$C_{2-12}$alkynyl" by itself or as part of another substituent, refers to an unsaturated hydrocarbyl group, which may be linear, or branched, comprising one or more carbon-carbon triple bonds. Preferred alkynyl groups thus comprise between 2 and 12 carbon atoms, preferably between 2 and 6 carbon atoms. Non limiting examples of $C_{2-12}$alkynyl groups include ethynyl, 2-propynyl, 2-butynyl, 3-butynyl, 2-pentynyl and its chain isomers, 2-hexynyl and its chain isomers and the like As used herein, the term "$C_{3-6}$cycloalkyl", by itself or as part of another substituent, refers to a saturated or partially saturated cyclic alkyl group containing from 3 to 6 carbon atoms. Examples of $C_{3-6}$cycloalkyl include cyclopropyl, cyclobutyl, cyclopentyl, and cyclohexyl. As used herein, the term "$C_{3-6}$cycloalkenyl", by itself or as part of another substituent, refers to a saturated or partially saturated cyclic alkenyl group containing from 3 to 6 carbon atoms. Examples of $C_{3-6}$cycloalkenyl include cyclopropenyl, cyclobutenyl, cyclopentenyl, and cyclohexenyl, As used herein, the term "$C_{6-16}$aryl", by itself or as part of another substituent, refers to a polyunsaturated, aromatic hydrocarbyl group having a single ring (i.e. phenyl) or multiple aromatic rings fused together (e.g. naphthalene), or linked covalently, typically containing 6 to 16 atoms; wherein at least one ring is aromatic. Aryl rings may be unsubstituted or substituted with from 1 to 4 substituents on the ring. Aryl may be substituted with halo, cyano, nitro, hydroxy, carboxy, amino, acylamino, alkyl, heteroalkyl, haloalkyl, phenyl, aryloxy, alkoxy, heteroalkyloxy, carbamyl, haloalkyl, methylenedioxy, heteroaryloxy, or any combination thereof. Examples of $C_{6-10}$aryl include phenyl, naphthyl, indanyl, 1,2,3,4-tetrahydro-naphthyl, and pyrenyl.

As used herein, the term "5- to 14-membered heteroaryl", by itself or as part of another substituent, refers to an aromatic monocyclic or polycyclic ring system comprising about 5 to about 14 ring atoms, preferably about 5 to about 10 ring atoms, in which one or more of the ring atoms is an element other than carbon, for example nitrogen, oxygen, sulfur, or a combination thereof. Examples of 5- to 14-membered heteroaryl include triazolyl, indolyl, The term "triazolyl" as used herein refers to 2H-1,2,3-triazolyl. Triazolyl may be substituted with halo, cyano, nitro, hydroxy, carboxy, amino, acylamino, alkyl, heteroalkyl, haloalkyl, phenyl, aryloxy, alkoxy, heteroalkyloxy, carbamyl, haloalkyl, methylenedioxy, heteroaryloxy, or any combination thereof.

Reference throughout this specification to "one embodiment" or "an embodiment" means that a particular feature, structure or characteristic described in connection with the embodiment is included in at least one embodiment envisaged herein. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are also envisaged herein, and form different embodiments, as would be understood by those in the art. For example, in the appended claims, any of the features of the claimed embodiments can be used in any combination.

Provided herein are fullerene compositions and methods of preparing thereof. The present compositions and methods are based on the finding by the present inventors that non-conjugated hydrophilic or amphiphilic polymers, which are functionalized with one or more functional groups capable of forming intermolecular interactions with fullerenes via pi-stacking, are surprisingly effective as carriers to disperse fullerenes in an aqueous environment, in particular when preparing fullerene-polymer compositions via mechanochemistry.

More particularly, the present application provides a method for the preparation of a fullerene-polymer composition, comprising:

(a) providing one or more fullerenes and a non-conjugated hydrophilic or amphiphilic polymer, said non-conjugated polymer comprising at least one substituent comprising a functional group capable of forming intermolecular interactions with the fullerene(s) via pi-stacking; and (b) mechanochemically treating the fullerene(s) and polymer, thereby obtaining a fullerene-polymer complex.

This will be explained further herein below.

The method described herein comprises providing one or more fullerenes. Accordingly, the method may comprise providing one type of fullerene or a mixture of different fullerenes. Methods for the preparation of fullerenes are well known in the art. For example, fullerenes can be produced in a reactor by vaporizing and condensing graphite in a helium atmosphere, as disclosed by Kratschmer et al. (*Nature* 1990, 347, 354-358).

Possible fullerenes include but are not limited to $C_{69}$, $C_{70}$, $C_{76}$, $C_{78}$, $C_{82}$, $C_{84}$, $C_{90}$, $C_{96}$, and $C_{120}$. Preferred fullerenes are the most stable forms $C_{60}$, and $C_{70}$. In particular embodiments, the one or more fullerenes comprise at least 90 wt %, at least 95wt %, or at least 99 wt % of $C_{60}$, $C_{70}$, or a mixture thereof. In certain embodiments, the one or more fullerenes comprise at least 90 wt %, at least 95wt %, or at least 99 wt % of $C_{60}$.

Optionally, the fullerene(s) may be substituted with one or more substituents, for example a substituent selected from $C_{1-20}$alkyl, $C_{1-20}$alkoxy, $C_{1-10}$aryl; which may further be functionalized with one or more functional groups such as amino or hydroxyl.

The method described herein further comprises providing a non-conjugated polymer, which may be a homopolymer or copolymer, comprising or substituted with at least one substituent comprising a functional group, wherein the functional group capable of forming intermolecular interactions with the fullerene(s) via pi-stacking ($\pi$-stacking). This means that the functional group comprises a pi-bond ($\pi$-bond) which can interact with pi-bonds of a fullerene, thereby forming an intermolecular attractive interaction (bond) between the polymer and the fullerene. Preferably, the pi-bond is a pi-bond between two carbon atoms.

Advantageously, said non-conjugated polymer as envisaged herein is a flexible polymer wherein the polymer backbone or polymer main chain, in particular the multiple repeating units (monomers) making up the polymer, do not form or do not comprise a conjugated system, or stated differently, when a monomer(s) or repeating unit(s) making up the polymer comprises at least one double bond, said at least one double bond of one monomer or repeating unit is isolated from the double bond or double bonds in the adjacent monomer(s) or repeating unit(s).

In particular embodiments, the functional group comprising a pi-bond is selected from the group consisting of $C_{2-12}$alkenyl, $C_{2-12}$alkynyl, $C_{6-16}$aryl, 5- to 14-membered heteroaryl, and $C_{3-6}$cycloalkenyl, optionally substituted with further substituents. In particular embodiments, the functional group is selected from $C_{2-6}$alkenyl and $C_{6-16}$aryl.

Non-limitative examples of suitable functional groups include, but are not limited to allyl (2-propenyl), propargyl (2-propynyl), phenyl, naphthyl, pyrenyl, vinyl, ethynyl, benzyl, anthryl, indolyl, imidazolyl, thienyl, pyrazinyl, pyrimidinyl, pyridazinyl, and triazolyl. Optionally, these functional groups may comprise further substituents, provided that the pi-bond still can interact with fullerenes.

In particular embodiments, the functional group is selected from allyl, propargyl, phenyl, phenyl, naphthyl, and pyrenyl.

The skilled person will understand that the functional group comprising a pi-bond should be positioned on the non-conjugated polymer such that it is available for interacting with a fullerene via pi-stacking. The present inventors have found that particularly good results are obtained when using a linear (i.e. non-branched) non-conjugated polymer, wherein at least one chain end (i.e. the $\alpha$ and/or $\omega$ end) of the polymer is provided with a functional group comprising a pi-bond as described above. Such polymers may be prepared via polymerization using an initiator and/or terminator which carries the functional group comprising a pi-bond as envisaged herein. In particular embodiments, only one chain end of the linear non-conjugated polymer is provided with a functional group comprising a pi-bond as described above.

Additionally or alternatively, one or more functional groups may be provided on the polymer on other positions, wherein multiple functional groups positioned on different monomers or repeating units making up the non-conjugated polymer do not form a conjugated system. In certain embodiments, the (co)polymer may be prepared using a monomer comprising the functional group, such that the functional group comprising a pi-bond is part of a repeating unit of the (co)polymer, provided that said functional groups on adjacent repeating units do not form a conjugated system. However, this is not critical to the present method. Indeed, a single functional group comprising a pi-bond as described herein can be sufficient. Accordingly, the non-conjugated polymer as envisaged herein may be a polymer substituted with one or more substituents carrying the functional group comprising a pi-bond as described above, but wherein the repeating unit or units as such do not carry the functional group as described above.

Accordingly, in certain embodiments, the non-conjugated polymer as envisaged herein comprises at most one functional group comprising a pi-bond as envisaged herein per repeating unit of the (co)polymer. Preferably, the non-conjugated polymer as envisaged herein comprises between 1 and 50, such as between 1 and 40 or between 1 and 30, of said functional groups per (co)polymer molecule. In particular embodiments, only one chain end of the linear non-conjugated polymer is provided with a functional group comprising a pi-bond as described above.

Because the non-conjugated polymer is provided with one or more functional groups as described above, the polymer and the fullerene can form intermolecular interactions, more particularly via pi-stacking, thereby forming a fullerene-polymer complex. This is different from fullerene-polymer complexes known in the art, which are solely based on other interactions such as charge transfer; or wherein fullerenes are enclosed in micelles formed by the polymer.

By choosing a hydrophilic or amphiphilic polymer, it can be ensured that the fullerene-polymer complex is sufficiently hydrophilic such that stable aqueous dispersions of the complex can be formed. If the non-conjugated polymer as envisaged herein is amphiphilic, the pi-bond comprising functional group is preferably provided on a hydrophobic part of the polymer. This promotes interaction between the hydrophobic part(s) with a fullerene, thereby allowing for the formation of a fullerene-polymer complex, while the hydrophilic part(s) of the amphiphilic polymer remain on the exterior of the complex, thus making the complex water-soluble.

By choosing a biocompatible polymer, the complex may be used in therapy.

In certain embodiments, the non-conjugated polymer, preferably linear polymer, as envisaged herein has a degree of polymerization of at least 20, 30, 40, 50, 60, 70, 80, 90 or 100.

Accordingly, the non-conjugated polymer used in the present method is hydrophilic or amphiphilic, and preferably biocompatible. In preferred embodiments, the polymer is selected from polyvinylpyrrolidone (PVP), poly(ethylene glycol) (PEG), a polymer produced from a cyclic imino ether, polyvinyl alcohol (PVA), a dextran, polyglutamic acid (PGA), a poly(oligo(ethylene glycol) acrylate) (POEGA), a poly(oligo(ethylene glycol) methacrylate) (POEGMA), and copolymers thereof. In particular embodiments, the polymer is selected from PVP, PEG, a polymer produced from a cyclic imino ether, poly[N-(2-hydroxypropyl)methacrylamide (PHPMA), and copolymers thereof.

In particular embodiments, the non-conjugated polymer may be a copolymer. Suitable copolymers may be random copolymers, block copolymers, or gradient copolymer. In particular embodiments, block copolymers or gradient copolymers may be used having two parts with different hydrophilicity, wherein the most hydrophobic part is provided with one or more functional groups capable of pi-stacking. The more hydrophobic part with functional group(s) can provide the required interaction between the polymer and fullerenes to obtain a fullerene/polymer complex, whereas the more hydrophilic part may facilitate dispersion of the complex in aqueous media. More particularly, amphiphilic copolymers may be used, wherein the hydrophobic part is provided with one or more functional groups capable of pi-stacking.

In particular embodiments, the non-conjugated polymer is a copolymer comprising at least one segment which is selected from the list comprising polyvinylpyrrolidone (PVP), poly(ethylene glycol) (PEG), a polymer produced from a cyclic imino ether, polyvinyl alcohol (PVA), a dextran, polyglutamic acid (PGA), a poly(oligo(ethylene glycol) acrylate) (POEGA), a poly(oligo(ethylene glycol) methacrylate) (POEGMA), and poly[N-(2-hydroxypropyl) methacrylamide (PHPMA). The other segments may comprise hydrophilic segments and/or hydrophobic segments, thereby obtaining a hydrophilic or amphiphilic polymer.

In particularly preferred embodiments, the non-conjugated polymer as envisaged herein further comprises an amide bond. Advantageously, a non-conjugated polymer comprising both a functional group with a pi-bond as envisaged herein and an amide bond, particularly an amide bond in proximity of said functional group with a pi-bond, has a higher affinity for the fullerene.

With "polyvinylpyrrolidone" or "PVP" herein is meant a polyvinylpyrrolidone comprising at least 50 wt % of vinylpyrrolidone monomers. The PVP may comprise up to 50 wt % of comonomers. In embodiments wherein the PVP is a copolymer, the copolymer preferably is a block copolymer or gradient copolymer. In particular embodiments, the PVP comprises at least 75, 80, or 90 wt % of vinylpyrrolidone monomers. In particular embodiments, the PVP is a homopolymer. In specific embodiments, the PVP is a homopolymer of formula (I):

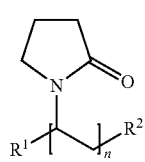

(I)

wherein n is the degree of polymerization, and wherein at least one of $R^1$ and $R^2$ comprises a functional group capable of interacting with fullerenes via pi-stacking. In particular embodiments, the degree of polymerization is between 10 and 500, for example about 50 or 100.

The term "polymer produced from a cyclic imino ether" as used herein refers to a polymer derived from a cyclic imino ether such as a 2-substituted 2-oxazoline, e.g. 2-ethyl-2-oxazoline or 2-methyl-2-oxazoline, preferably via ring opening polymerization. More particularly, such polymers are typically prepared from at least 50 wt % of a cyclic imino ether of formula (II):

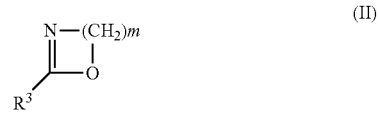

(II)

wherein m is an integer ranging from 2 to 5; and wherein $R^3$ preferably is selected from $C_{1-4}$alkyl, $C_{1-4}$alkenyl, $C_{1-4}$alkynyl, $C_{6-16}$aryl, $C_{3-6}$cycloalkyl or hydrogen. In particular embodiments, $R^3$ is selected from $C_{1-3}$alkyl, $C_{1-3}$alkenyl, $C_{1-3}$alkynyl, $C_{6-10}$aryl, and hydrogen. In particular embodiments, $R^3$ is methyl or ethyl. This results in water-soluble polymers or polymer parts. In certain embodiments, $R^3$ is butenyl or butynyl. This provides pi-bonds which can interact with fullerenes via pi-stacking.

In preferred embodiments, m is 2 or 3; in particularly preferred embodiments, m is 2. If m is 2, the resulting polymer is a polyoxazoline. If m is 3, the resulting polymer is a polyoxazine.

In particular embodiments, the degree of polymerization of the polymer produced from a cyclic imino ether is between 10 and 500, for example about 50 or 100.

Polymers produced from a cyclic imino ether for use in the present methods may be prepared from mixtures of monomers of formula (II) having a different substituent $R^3$, or all monomers may be provided with the same substituent $R^3$.

The term "polymer produced from a cyclic imino ether" as used herein also includes polymers prepared from at least 50 wt % of a cyclic imino ether of formula (II) wherein m and $R^3$ are the same as described above, and wherein one or more hydrogen atoms in the $(CH2)_m$ moiety can each independently be replaced by a substituent selected from $C_{1-4}$alkyl, $C_{1-4}$alkenyl, $C_{1-4}$alkynyl, $C_{6-16}$aryl, and $C_{3-6}$cycloalkyl.

The polymer produced from a cyclic imino ether may comprise up to 50 wt % of comonomers. In embodiments wherein the polymer produced from a cyclic imino ether is a copolymer, the copolymer preferably is a block copolymer or gradient copolymer. In particular embodiments, the polymer produced from a cyclic imino ether is produced from at least 75, 80, or 90 wt % of monomers of formula (II). In particular embodiments, the polymer produced from a cyclic imino ether is a homopolymer. In specific embodiments, the polymer produced from a cyclic imino ether is a homopolymer of formula (III):

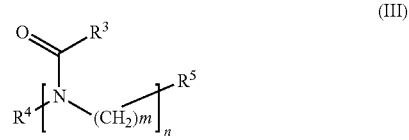

(III)

wherein n is the degree of polymerization; and wherein m and $R^3$ have the same meaning as described above; and at least one of $R^3$, $R^4$ and $R^5$ comprises a functional group capable of interacting with fullerenes via pi-stacking. In particular embodiments, the degree of polymerization is between 10 and 500, for example about 50 or 100.

With "poly(ethylene glycol)" or "PEG" herein is meant a PEG prepared from at least 50 wt % of ethylene glycol monomers. The PEG may comprise up to 50 wt % of comonomers. In embodiments wherein the PEG is a copolymer, the copolymer preferably is a block copolymer or gradient copolymer. In particular embodiments, the PEG comprises at least 75, 80, or 90 wt % of ethylene glycol monomers. In particular embodiments, the PEG is a homopolymer. In specific embodiments, the PEG is a homopolymer of formula (IV):

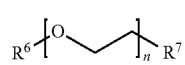

(IV)

wherein n is the degree of polymerization, and at least one of $R^6$ and $R^7$ comprises a functional group capable of interacting with fullerenes via pi-stacking. In particular embodiments, the degree of polymerization is between 10 and 500, for example about 50 or 100.

The fullerene(s) and the non-conjugated polymer(s) are preferably provided in a fullerene:polymer molar ratio between 0.1 and 10. In particular embodiments, the fullerene:polymer molar ratio ranges from 0.2 to 5. In certain embodiments, the fullerene:polymer molar ratio ranges from 0.5 to 2. The optimal fullerene:polymer molar ratio may depend on various parameters such as the polymer type, the degree of polymerization, and the amount of functional groups capable of pi-stacking.

With "polyvinyl alcohol" or "PVA" herein is meant a polyvinyl alcohol comprising at least 50 wt % of vinyl alcohol monomers. The PVA may comprise up to 50 wt % of comonomers. In embodiments wherein the PVA is a copolymer, the copolymer preferably is a block copolymer or gradient copolymer. In particular embodiments, the PVA comprises at least 75, 80, or 90 wt % of vinyl alcohol monomers. In particular embodiments, the PVA is a homopolymer. In particular embodiments, the degree of polymerization is between 10 and 500, for example about 50 or 100.

With "polyglutamic acid" or "PGA" herein is meant a polyglutamic acid comprising at least 50 wt % of glutamic acid monomers. The PGA may comprise up to 50 wt % of comonomers. In embodiments wherein the PGA is a copolymer, the copolymer preferably is a block copolymer or gradient copolymer. In particular embodiments, the PGA comprises at least 75, 80, or 90 wt % of glutamic acid monomers. In particular embodiments, the PGA is a homopolymer. In particular embodiments, the degree of polymerization is between 10 and 500, for example about 50 or 100.

With "poly(oligo(ethylene glycol) acrylate)" or "POEGA" herein is meant a poly(oligo(ethylene glycol) acrylate) comprising at least 50 wt % of oligo(ethylene glycol) acrylate monomers. The POEGA may comprise up to 50 wt % of comonomers. In embodiments wherein the POEGA is a copolymer, the copolymer preferably is a block copolymer or gradient copolymer. In particular embodiments, the POEGA comprises at least 75, 80, or 90 wt % of oligo(ethylene glycol) acrylate monomers. In particular embodiments, the POEGA is a homopolymer. In particular embodiments, the degree of polymerization is between 10 and 500, for example about 50 or 100.

With "poly(oligo(ethylene glycol) methacrylate)" or "POEGMA" herein is meant a poly(oligo(ethylene glycol) methacrylate) comprising at least 50 wt % of oligo(ethylene glycol) methacrylate monomers. The POEGMA may comprise up to 50 wt % of comonomers. In embodiments wherein the POEGMA is a copolymer, the copolymer preferably is a block copolymer or gradient copolymer. In particular embodiments, the POEGA comprises at least 75, 80, or 90 wt % of oligo(ethylene glycol) methacrylate monomers. In particular embodiments, the POEGMA is a homopolymer. In particular embodiments, the degree of polymerization is between 10 and 500, for example about 50 or 100.

With "poly[N-(2-hydroxypropyl)methacrylamide]" or "PHPMA" herein is meant a poly[N-(2-hydroxypropyl)methacrylamide] comprising at least 50 wt % of N-(2-hydroxypropyl)methacrylamide monomers. The PHPMA may comprise up to 50 wt % of comonomers. In embodiments wherein the PHPMA is a copolymer, the copolymer preferably is a block copolymer or gradient copolymer. In particular embodiments, the PHPMA comprises at least 75, 80, or 90 wt % of N-(2-hydroxypropyl)methacrylamide monomers. In particular embodiments, the PHPMA is a homopolymer. In particular embodiments, the degree of polymerization is between 10 and 500, for example about 50 or 100.

With "dextran" herein is meant a member of a group of polysaccharides which are composed of glucose monomers linked predominantly via α-1,6 glycosidic linkages, optionally with α-1,3 branches.

In particular embodiments, the fullerene(s) and the non-conjugated polymer(s) are provided in a fullerene:polymer weight ratio between 1:100 and 3:20.

In the present method, the fullerene(s) and non-conjugated polymer(s) described above are mechanochemically treated as to obtain a fullerene-polymer complex. Accordingly, the fullerene-polymer complex is obtained via (only) mechanical action. The mechanochemical treatment allows for obtaining a homogeneous fullerene-polymer mixture. Due to the possibility of the non-conjugated polymer to interact with the fullerene(s) via pi-stacking, a fullerene-polymer complex is obtained, more specifically a particulate fullerene-polymer complex.

An advantage of mechanochemical treatment of fullerenes and polymers as described herein is that no solvent is required for obtaining the fullerene-polymer complex. This allows for eliminating potential issues related to the use of solvents, such as toxicity, waste, and costs. Accordingly, in preferred embodiments, step (b) of the present method is performed in the absence of solvents, more particularly in the absence of liquids. This means that preferably no solvents are added to the fullerene(s) and polymer(s) prior to or during mechanochemical treatment.

Preferably, the mechanochemical treatment of the fullerene(s) and polymer(s) involves grinding or milling of the fullerene-polymer mixture. Grinding or milling allows for obtaining highly homogeneous fullerene-polymer compositions in the form of particles. Typically, the particles are nanoparticles having a size below 200 nm (see further).

The inventors have found that initially increasing the grinding or milling time increases the particle yield, while after prolonged grinding or milling the yield increases slower or even decreases. Typically, the grinding or milling is performed over a period between 1 minute and 24 hours, more particularly between 2 minutes and 60 minutes. The optimal grinding or milling time can be device and frequency dependent.

In particularly preferred embodiments, the mechanochemical treatment for preparing the fullerene-polymer mixture involves ball milling. Ball milling may generally be performed using a mill wherein a charge of grinding balls (or grinding media having other shapes) is confined in a container therefore. More particularly, ball milling may be performed using a conventional ball mill comprising a hollow cylindrical shell rotating around its axis, or in other types of grinding or milling equipment such as vibratory or planetary ball mills. In specific embodiments, the mechanochemical treatment may involve vibration milling, more particularly high speed vibration milling (HSVM). The inventors have found that vibration milling provides particularly good results, and can results in particles having a size below 100 nm. For HSVM, a milling time between 1 minute and 4 hours was found to provide the best results. Preferably, a grinding or milling time between 5 and 60 minutes is chosen, for example about 10 minutes.

In certain embodiments, the mechanochemical treatment of the fullerene(s) and non-conjugated polymer(s) involves extrusion of the fullerene-polymer mixture, for example using a so-called "mini-extruder".

Although the mechanochemical treatment can allow for obtaining nanoparticles having a well-defined size, the method described herein may further comprise a step (c) of purifying the fullerene-polymer complex obtained via the mechanochemical treatment described above.

In preferred embodiments, the fullerene/polymer composition obtained via mechanical treatment is dispersed in the desired aqueous medium (e.g. water). Dispersion of the composition into the aqueous medium can be facilitated through shaking, sonication, or other techniques known in the art. Particles or particle clusters which are too large for forming stable dispersions may be removed by letting these particles precipitate from the dispersion, followed by separating the precipitate (comprising the particles which are too large) and the supernatant (comprising the smaller nanoparticles). Precipitation can be facilitated via centrifugation, as is known in the art.

Additionally or alternatively, the fullerene-polymer complex may be filtered, preferably using a porous membrane filter having a pore size below 0.5 µm, for example about 0.2 µm. This allows for removing large aggregates of the fullerene-polymer particles. Typically, filtration is performed on the particles when dispersed in a liquid (aqueous medium).

Further provided herein are fullerene-polymer compositions obtainable using the method described above. More particularly, provided herein is a composition comprising a fullerene-polymer complex comprising at least one fullerene and a non-conjugated hydrophilic polymer as described above. In the particles, the fullerene(s) and polymer(s) interact via pi-stacking.

In particular embodiments, the fullerene:polymer molar ratio of the fullerene(s) and polymer(s) within the composition is between 0.1 and 10, preferably between 0.2 and 5.

In particular embodiments, the particles have a number average particle size between 10 nm and 200 nm. In further embodiments, the particles have a number average particle size between 50 nm and 100 nm. In particular embodiments, at least 90% of the particles have a particle size below 100 nm. The particle sizes referred to herein are hydrodynamic sizes as measured via dynamic light scattering (DLS). For the size measurement, the particles are preferably suspended in (distilled) water at 25° C. at a suitable particle concentration as known by the skilled person, for example about 1.0 g/L.

The fullerene-polymer complexes prepared according to the method described herein can be used to form stable dispersions in aqueous media. As used herein, the term "stable dispersion" refers to a dispersion or suspension wherein less than 1 wt % of the dispersed particles precipitate at about 25° C. for at least 1 day, preferably at least 5 days.

Accordingly, in particular embodiments, the fullerene-polymer complex (in the form of particles) is dispersed or suspended in an aqueous medium, more particular in an aqueous liquid, thus forming an aqueous composition. In particular embodiments, the aqueous composition comprises at least 1 wt % of fullerenes, preferably at least 1.5 wt %, more preferably at least 2 wt % fullerenes, for example about 5 wt % fullerenes.

In certain embodiments, the aqueous composition comprises at least 50 wt % water, more particularly at least 75%, and preferably at least 90 wt % water.

In particular embodiments, an aqueous composition as envisaged herein comprises:
at least 2 wt % of fullerenes;
at least 1 wt % of non-conjugated polymers comprising a functional group comprising a pi-bond as envisaged herein; and
at least 75 wt % of water.

In preferred embodiments, the fullerenes comprise at least 50 wt % $C_{60}$.

The compositions comprising a fullerene-polymer complex described herein may be useful in medicine. For example, in view of the fact that fullerenes can function as photosensitizer, the compositions described herein may be useful in photodynamic therapy, e.g. for the treatment of cancer. As a further example, due to the ability of fullerenes to scavenge reactive oxygen species, the compositions may be used for the treatment or prevention of diseases which are associated to oxidative stress, such as Parkinson's disease, Alzheimer's disease, cardiovascular diseases, arthritis, and cancer. Examples of cardiovascular diseases which may be treated or prevented using compositions as described herein include but are not limited to atherosclerosis, hypertension, and heart failure.

The specific fullerene-polymer complexes described herein may allow for an excellent stability and biocompatibility, which can increase the effectiveness of the fullerenes comprised therein for the treatment of the above-mentioned therapies. Depending on the envisaged treatment, the administration of the composition to a patient in need thereof may be topical, intravenous, or oral.

Further provided herein is the use of a non-conjugated polymer as described herein for increasing the solubility of a fullerene in aqueous media, more particularly water. The solubilization of fullerenes in water is particularly important for the use of fullerenes for biomedical applications.

The solubilization of fullerenes in water is further relevant for the use of fullerenes as antioxidants. Accordingly, further provided herein is the use of compositions as described herein as antioxidant, for example in personal care products such as skin creams, cosmetic applications, and food additives.

Further provided herein is the use of compositions as described herein in personal care products, cosmetic applications, and food additives.

EXAMPLES

The following examples are provided for the purpose of illustrating the claimed methods and applications and by no means are meant and in no way should be interpreted to limit the scope of the present invention.

Example 1

Polyoxazoline Polymers Having a Functional Group Comprising pi-Bonds 1.1 Materials and Methods High Speed Vibration Milling (HSVM) was performed using a Fritsch Mini-Mill Pulverisette 23 in a 10 mL stainless steel grinding bowl with a 15 mm diameter stainless steel grinding ball. Typically, a milling time of 10 minutes was used.

Dynamic Light Scattering (DLS) measurements were executed on a Zetasizer Nano-ZS Malvern apparatus (Malvern Instruments Ltd) using disposable cuvettes. The excitation light source was a HeNe laser at 633 nm and the intensity of the scattered light was measured at an angle of 173°. All measured dispersions had a concentration of 1.0 mg/mL in deionized water and were filtered through Millipore membranes (pore size 0.2 µm) prior to measurement. The samples were incubated for at least 120 seconds to reach equilibrium. Deionized water with a resistivity less than 18.2 MΩ·cm was prepared using a Sartorius Arium 611 with the Sartopore 2150 (0.45+0.2 µm pore size) cartridge filter. This method measures the rate of the intensity fluctuation and the size of the particles is determined through the Stokes-Einstein equation.

UV-VIS spectra were recorded on a Varian Cary 100 Bio UV-VIS spectrophotometer equipped with a Cary temperature and stir control. Samples were measured in either quartz or disposable cuvettes with a pathlength of 1.0 cm in the wavelength range of 200 to 700 nm. The concentration of each sample was 1.0 mg/ml in milliQ water.

Lyophilisation was performed on a Martin Christ freeze-dryer, model Alpha 2-4 LSCplus.

Size-exclusion chromatography (SEC) was performed on a Agilent 1260-series HPLC system equipped with a 1260 online degasser, a 1260 ISO-pump, a 1260 automatic liquid sampler (ALS), a thermostatted column compartment (TCC) at 50° C. equipped with two PLgel 5 µm mixed-D columns and a precolumn in series, a 1260 diode array detector (DAD) and a 1260 refractive index detector (RID). The used eluent was DMA containing 50 mM of LiCl at a flow rate of 0.500 ml/min. The spectra were analysed using the Agilent Chemstation software with the GPC add on. Molar mass values and Ð (polydispersity) values were calculated against PMMA standards from PSS.

Proton nuclear magnetic resonance spectra ($^1$H NMR) were recorded on a Bruker Avance 300 or 400 MHz spectrometer at room temperature. The chemical shifts are given in parts per million (δ) relative to TMS. The compounds were dissolved in either CDCl$_3$, D$_2$O or DMSO-d6 from Eurisotop.

Matrix assisted laser desorption/ionization time of flight mass spectroscopy (MALDI-TOF MS) was performed on an Applied Biosystems Voyager De STR MALDI-TOF mass spectrometer equipped with 2 m linear and 3 m reflector flight tubes, and a 355 nm Blue Lion Biotech Marathon solid state laser (3.5 ns pulse). All mass spectra were obtained with an accelerating potential of 20 kV in positive ion mode and in either reflectron or linear mode.

The polymerizations were performed in capped vials in a single mode microwave Biotage initiator sixty (IR temperature sensor) (Biotage, Uppsala, Sweden).

Samples were measured with GC to determine the monomer conversion from the ratio of the integrals from the monomer and the reaction solvent. GC was performed on an Agilent 7890A system equipped with a VWR Carrier-160 hydrogen generator and an Agilent HP-5 column of 30 m length and 0.320 mm diameter. An FID detector was used and the inlet was set to 250° C. with a split injection of ratio 25:1. Hydrogen was used as carrier gas at a flow rate of 2 mL/min. The oven temperature was increased with 20° C./min from 50° C. to 120° C., followed by a ramp of 50° C./min to 300° C.

Unless otherwise stated, all chemicals were used as received. All HPLC grade solvents were purchased from Sigma-Aldrich (acetone, diethylether, DMA, ethyl acetate, dichloromethane, methanol, acetonitrile). C$_{60}$ (purity 99,5%) was purchased from Sigma Aldrich.

1.2 Polyoxazoline Synthesis

Poly(2-ethyl-2-oxazoline) and poly(2-methyl-2-oxazoline) were prepared via cationic ring polymerization. The preparation of polyoxazolines via cationic ring polymerization is well-known in the art, for example from Fijten et al. (*Macromol. Chem. Phys.* 2008, 209, 1887-1895). The polymerization was performed using a propargyl-containing initiator, more particularly propargyl tosylate and propargyl benzenesulfonate. The polymerization reaction was ended by addition of tetramethyl amonium hydroxide, resulting in a hydroxyl end-group.

The PAOx polymers were prepared under inert atmosphere by preparing a 4M monomer solution in acetonitrille with an appropriate amount of initiator for the preparation of polymers with 20, 50 or 100 repeating units. Next the monomer solution was heated in a biotage microwave to 140° C. for 3.5, 8 or 16 min to reach near full monomer conversion. After the polymerization, a slight excess of terminator was added to introduce the desired functionality on the polymer. Next the polymers were isolated from diethylether, after which they were dissolved in water and freeze dried. The polymers were characterized by MALDI-TOF-MS, SEC and $^1$HNMR.

This way, poly(2-ethyl-2-oxazoline) and poly(2-methyl-2-oxazoline) were obtained wherein one chain end is provided with a propargyl functionality while the other chain end is provided with a hydroxyl functionality. The propargyl-containing chain end has a high affinity for fullerenes, thus allowing for the use of the polymers for preparing fullerene-polymer complexes as described herein. These poly(2-ethyl-2-oxazoline) and poly(2-methyl-2-oxazoline) polymers are further referred to herein as "propargyl-PEtOx-OH" and "propargyl-PMEtOx-OH", respectively.

Similarly, polyoxazoline polymers were prepared without the use of initiators or terminators having pi-bonds. Suitable preparation methods are described by Hoogenboom et al. (*J. Polym. Sci. A Polym. Chem.* 2007, 45, 416-422; and *Macromolecules* 2008, 41, 1581-1583). In order to enable pi-stacking, these polymers were prepared from monomers having a functional group comprising pi-bonds. More particularly, block and gradient copolymers were prepared comprising of poly(2-methyl-2-oxazoline) (degree of polymerization of 75) and poly(2-phenyl-2-oxazoline) (degree of polymerization of 25).

1.3 C$_{60}$-Nanoparticle Preparation and Analysis

C$_{60}$ polymer nanoparticles (NPs) were prepared in the following manner. First, C$_{60}$ and the polymer were weighed and poured in the mixing vessel in either a 1:2, 1:1 or a 2:1 molar ratio. Next, the solid mixture was milled for 10 min at 50 Hz, after which a brown to black solid was obtained. To extract the C$_{60}$ polymer NPs, 2 ml of water were added to the mixing vessel after which it was milled again at 50 Hz for 2 min to obtain a dark solution. This solution was then filtered through a 200 nm pore size filter to remove any undissolved $C_{60}$. The obtained solution was then freeze-dried and the NPs were characterized by UV-VIS spectroscopy and dynamic light scattering.

UV-VIS spectroscopy was performed on the samples to analyze the $C_{60}$ content. To this end, stock solutions of the $C_{60}$ polymer NPs were prepared of 1 mg/ml in miliQ water, which were then diluted either 5 or 10 times to obtain an absorption in the range of 0-2 absorbance units. After correction for a blank, the concentrations were calculated using the Lambert-Beer law with the known extinction coefficient from literature ($\varepsilon$=49000).

Dynamic light scattering was performed on $C_{60}$ polymer NPs solutions of 1 mg/ml. After the preparations of the solutions, the solutions were filtered and measured. The measurements were performed with either miliQ water or PBS-buffer as a solvent. The equilibration time was 180 s and temperature was 25° C. 3 runs were performed on each sample.

1.4 Results and Discussion

Fullerene-Polymer nanoparticle (NP) compositions were prepared via HSVM using different polymers and fullerene:polymer ratios. The basic structure of the polyaxozoline polymers (1-5) used in the present example are shown in FIG. 1. Polymers 1-5 each comprise one or more functional groups (propargyl, ethenyl, phenyl) which are capable of interacting with fullerenes via pi-stacking. Polymer 6 which does not comprise such functional group was used as reference.

Parameters which were varied include the degree of polymerization (DP) of the polyoxazoline polymer and the molar ratio of fullerene to polymer. Table 1 provides an overview of the experiments which were performed.

For each experiment, the size of the obtained particles was measured via DLS, the amount of $C_{60}$ (wt %) which can be dispersed in water, the particle yield (i.e. the particle fraction remaining in aqueous phase after filtration through a 0.2 µm pore size filter), the particle dispersity, and the particle stability. Dispersity was assessed through DLS, which gives a dispersity on the particle size. The stability of the nanoparticles was examined by remeasuring the solutions in an interval of 7 days over the course of 4 months.

The results are provided in Table 1. All experiments with polymers 1-5 were found to lead to fullerene:polymer nanoparticles having an average particle size below 100 nm with a good particle dispersity (<0.3) (i.e. a population of very defined NPs); and to allow for obtaining $C_{60}$ concentrations in water of 1.5 wt %.up to 8.7 wt %. Even at such high concentrations, the dispersions were stable for weeks to months.

In contrast, no stable dispersions could be formed with polymer 6 without pi-bond containing functional groups. This clearly shows that polymers having pi-bond containing groups capable of pi-stacking provide much better results for the preparation of aqueous fullerene dispersions using mechanochemistry.

TABLE 1

Overview of polyoxazoline:$C_{60}$ experiments

| Polymer | DP | Molar ratio $C_{60}$:polymer | Particle size (nm) | NP $C_{60}$ wt % | NP yield (%) | NP dispersity | NP stability (weeks) |
|---|---|---|---|---|---|---|---|
| 1 | 50 | 0.5:1 | 45 | 3.2 | 53 | 0.177 | 8 |
| 1 | 50 | 1:1 | 65 | 6.8 | 60 | 0.214 | 8 |
| 1 | 50 | 2:1 | 82 | 8.6 | 42 | 0.253 | 4 |
| 1 | 100 | 0.5:1 | 70 | 1.5 | 50 | 0.136 | >16 |
| 1 | 100 | 1:1 | 72 | 5.5 | 92 | 0.101 | 12 |
| 1 | 100 | 2:1 | 73 | 8.7 | 78 | 0.124 | >16 |
| 2 | 80:20 | 0.5:1 | 48 | 1.5 | 45 | 0.244 | 8 |
| 3 | 75:25 | 0.5:1 | 40 | 3.1 | 97 | 0.142 | >16 |
| 4 | 75:25 | 0.5:1 | 41 | 2.8 | 90 | 0.179 | >16 |
| 5 | 100 | 0.5:1 | 85 | 3.6 | 88 | 0.269 | >4 |
| 5 | 100 | 1:1 | 77 | 5.5 | 70 | 0.220 | >4 |
| 6 | 100 | 0.5:1 | N/A | N/A | N/A | N/A | 0 |

A MTT toxicity assay showed that NPs comprising $C_{60}$ complexed with polyoxazoline polymers with a naphtyl or pyrenyl functional group at one end of the polymer had a similar effect on cell viability as the polyoxazoline polymers without fullerene. NPs comprising $C_{60}$ complexed with polyoxazoline polymers with a allyl, propargyl or phenyl functional group showed a cell viability of at least 80% for $C_{60}$ concentrations up to about 20 to 50 µM.

1.5 $C_{70}$-Polyoxazoline Nanoparticle Preparation and Analysis $C_{70}$ polymer nanoparticles (NPs) were prepared using a similar procedure as in section 1.3 above. $C_{70}$ and a polyoxazoline polymer were weighed and poured in the mixing vessel in a 2:1 molar ratio.

Next, the solid mixture was milled for 10 min at 50 Hz, after which a brown to black solid was obtained. To extract the $C_{70}$ polyoxazoline NPs, 2 ml of water were added to the mixing vessel after which it was milled again at 50 Hz for 2 min to obtain a dark solution. This solution was then filtered through a 200 nm pore size filter to remove any undissolved $C_{70}$. The obtained solution was then freeze-dried and the NPs were characterized by UV-VIS spectroscopy and dynamic light scattering, as described in section 1.3 above.

The results are shown in Table 2.

TABLE 2

Polyoxazoline:$C_{70}$ nanoparticles

| polymer | NP $C_{70}$ Wt % | NP Yield (%) | Size | PDI (NP dispersity) |
|---|---|---|---|---|
| (structure with R1 = allyl) | 2.01 | 50.2 | 32 | 0.297 |
| (structure with R1 = propargyl) | 3.99 | 97.3 | 39 | 0.164 |

TABLE 2-continued

Polyoxazoline:C70 nanoparticles

| polymer | NP C70 Wt % | NP Yield (%) | Size | PDI (NP dispersity) |
|---|---|---|---|---|
| 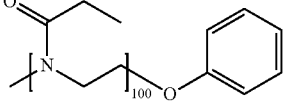 | 3.50 | 85.9 | 21.9 | 0.506 |

Example 2

PEG Modification

Materials and methods used were generally as in example 1, section 1.1 above.

Commercial monomethylether polyethyleneglycol (PEG) was used to synthesize modified PEGs comprising a functional group having pi-bonds. Two procedures were used. A first procedure entails the deprotonation of the hydroxyl functionality of PEG using 1.6 molar equivalents of NaH in dry THF, followed by the dropwise addition of 3 molar equivalents of the desired brominated functionality.

The second procedure requires the conversion of the hydroxyl functionality to the respective tosylate by adding 13 molar equivalents of tosylchloride to a basic solution of polymer in dichloromethane. Following the isolation of the modified PEG polymer by precipitation in diethylether, the tosylated polymer was then reacted overnight with 10 molar equivalents of the alkoxide of the desired functionality.

The final polymers were all isolated by precipitation in diethylether, followed by resuspension in water and then dialyzed for at least 3 days. Finally, the polymers were characterized by MALDI-TOF-MS, SEC and $^1$HNMR.

$C_{60}$ polymer nanoparticles comprising the modified PEG were prepared (in a $C_{60}$:polymer ratio of 1:2) and analysed as in example 1, section 1.3 above. Results are shown in Table 3.

TABLE 3

PEG:$C_{60}$ nanoparticles, with row 1-3 corresponding to a PEG with functional group, and row 4 corresponding to the unmodified PEG

| polymer | Size | PDI (NP dispersity) |
|---|---|---|
| 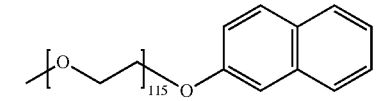 | 51.7 | 0.298 |
| 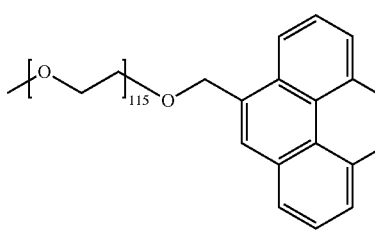 | 73.3 | 0.154 |

TABLE 3-continued

PEG:$C_{60}$ nanoparticles, with row 1-3 corresponding to a PEG with functional group, and row 4 corresponding to the unmodified PEG

| polymer | Size | PDI (NP dispersity) |
|---|---|---|
| 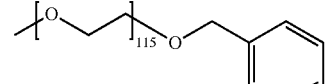 | 116.9 | 0.344 |
| 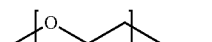 | 80.8 | 0.4 |

This clearly shows that polymers having pi-bond containing groups capable of pi-stacking (row 1-3) provide much better results for the preparation of aqueous fullerene dispersions using mechanochemistry.

Example 3

PVP Polymers

Materials and methods used were generally as in example 1, section 1.1 above.

N-vinylpyrrolidone was prior to the polymerization distilled. Next, a 3M monomer (M) solution was prepared by diluting the monomer in anisole, followed by the addition of chain transfer agent (CTA) and initiator(AIBN) in the following molar ratio [M]:[CTA]:[AIBN]=150:1:0.3. The polymerization mixture was then degassed by performing at least 3 freeze-thaw cycles. Next, the polymerization mixture was heated to 70° C. and the conversion was followed by gas chromatography until the desired conversion was reached, after which the polymerization mixture was cooled down and opened to the air. The polymers were then isolated by precipitation in diethylether, followed by resuspension in water and dialysis.

$C_{60}$ polymer nanoparticles comprising the PVP polymers were prepared (in a $C_{60}$:PVP ratio of 2:1) and analysed as in example 1, section 1.3 above. The results are shown in Table 4.

TABLE 4

PVP:$C_{60}$ nanoparticles, for PVP with aromatic functional group (row 1 + 2) and PVP without aromatic functional group (row 3 + 4)

| polymer | NP $C_{60}$ Wt % | NP Yield (%) | Size | PDI |
|---|---|---|---|---|
| 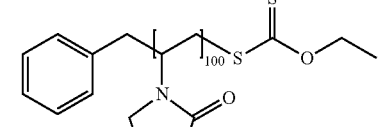 | 1.63 | 49.1 | 77.3 | 0.25 |
| 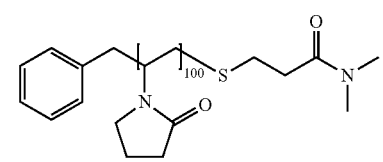 | 2.65 | 84.4 | 74.8 | 0.235 |

TABLE 4-continued

PVP:C$_{60}$ nanoparticles, for PVP with aromatic functional group
(row 1 + 2) and PVP without aromatic functional group (row 3 + 4)

| polymer | NP C$_{60}$ Wt % | NP Yield (%) | Size | PDI |
|---|---|---|---|---|
| [structure] | 0.58 | 17.6 | 48.0 | 0.47 |
| [structure] | 0.65 | 20.1 | 71.0 | 0.256 |

In contrast to PVP polymers without an aromatic group, the PVP polymers comprising an aromatic group allowed to obtain fullerene:polymer nanoparticles in a high yield, having an average particle size below 100 nm with a good particle dispersity (<0.3). This clearly shows that polymers having pi-bond containing groups capable of pi-stacking provide much better results for the preparation of aqueous fullerene dispersions using mechanochemistry.

What is claimed is:

1. A composition comprising a fullerene-polymer complex comprising one or more fullerenes and a non-conjugated hydrophilic or amphiphilic polymer, said non-conjugated polymer being substituted with at least one substituent comprising a functional group comprising a carbon-carbon pi-bond which interacts with said one or more fullerenes via pi-stacking.

2. The composition according to claim 1, wherein said functional group is selected from the group consisting of allyl, propargyl, phenyl, naphthyl, pyrenyl, vinyl, ethynyl, benzyl, anthryl, indolyl, imidazolyl, thienyl, pyrazinyl, pyrimidinyl, piridazinyl, and triazolyl.

3. The composition according to claim 1, wherein said non-conjugated polymer is a linear polymer wherein at least one chain end of said linear polymer is provided with said functional group.

4. The composition according to claim 1, wherein said non-conjugated polymer is selected from the group consisting of polyvinylpyrrolidone (PVP), poly(ethylene glycol) (PEG), a polymer produced from a cyclic imino ether, polyvinyl alcohol (PVA), a dextran, polyglutamic acid (PGA), a poly(oligoethylene glycol) acrylate) (POEGA), a poly(oligoethylene glycol methacrylate) (POEGMA), poly [N-(2-hydroxypropyl)methacrylamide (PHPMA), and copolymers thereof.

5. The composition according claim 1 wherein said non-conjugated polymer further comprises an amide bond.

6. The composition according to claim 1, wherein said fullerene-polymer complex is provided as particles having an average size between 25 nm and 100 nm as measured via dynamic light scattering.

7. The composition according to claim 1 wherein said fullerene-polymer complex is suspended in an aqueous solvent, and wherein said composition comprises at least 1 wt % of said one or more fullerenes.

8. The composition according to claim 1, wherein said one or more fullerenes comprise at least 90 wt % C$_{60}$.

9. A medicament comprising the composition according to claim 1.

10. A method for the treatment of an oxidative damage-related diseases or disorder comprising administering a composition according to claim 1 to a patient in need thereof.

11. An antioxidant composition comprising a composition according to claim 1.

12. A method for the preparation of the composition according to claims 1, comprising:
(a) providing one or more fullerenes and a non-conjugated hydrophilic or amphiphilic polymer, said non-conjugated polymer being substituted with at least one substituent comprising a functional group comprising a carbon-carbon pi-bond capable of interacting with said fullerene via pi-stacking; and
(b) mechanochemically treating said fullerene and said non-conjugated polymer, thereby obtaining a fullerene-polymer complex.

13. The method according to claim 12, wherein step (b) comprises milling said fullerene and said non-conjugated polymer.

14. The method according to claim 12, wherein said functional group is selected from the list consisting of allyl, propargyl, phenyl, naphthyl, and pyrenyl.

15. The method according to claim 12, wherein step (b) is performed in the absence of solvents.

16. A method for increasing the solubility of fullerenes in water, comprising forming a complex between a fullerene and a non-conjugated polymer, wherein said non-conjugated polymer is substituted with at least one substituent comprising a functional group comprising a carbon-carbon pi-bond capable of interacting with said fullerene via pi-stacking.

17. The method of claim 10, wherein the oxidative damage-related disease or disorder is selected from the group consisting of Parkinson's disease, Alzheimer's disease, cardiovascular diseases, and cancer.

18. The method of claim 13, wherein the milling is performed using High Speed Vibration Milling.

* * * * *